(12) United States Patent
Chu et al.

(10) Patent No.: US 11,326,054 B2
(45) Date of Patent: May 10, 2022

(54) POLYMERS COMPRISING 1,3-CYCLOBUTANE DIMETHANOL (CBDO-1)

(71) Applicants: Qianli Chu, Grand Forks, ND (US); Rahul Shahni, Grand Forks, ND (US)

(72) Inventors: Qianli Chu, Grand Forks, ND (US); Rahul Shahni, Grand Forks, ND (US)

(73) Assignee: The University of North Dakota, Grand Forks, ND (US)

( * ) Notice: Subject to any disclaimer, the term of this patent is extended or adjusted under 35 U.S.C. 154(b) by 0 days.

(21) Appl. No.: 17/001,966

(22) Filed: Aug. 25, 2020

(65) Prior Publication Data

US 2022/0025173 A1 Jan. 27, 2022

Related U.S. Application Data

(63) Continuation-in-part of application No. 16/934,390, filed on Jul. 21, 2020, now abandoned.

(51) Int. Cl.
| | | |
|---|---|---|
| *C08G 63/193* | (2006.01) | |
| *C08L 67/02* | (2006.01) | |
| *C08G 63/199* | (2006.01) | |
| C08K 3/22 | (2006.01) | |
| C08K 5/57 | (2006.01) | |

(52) U.S. Cl.
CPC ............ *C08L 67/02* (2013.01); *C08G 63/193* (2013.01); *C08G 63/199* (2013.01); C08K 3/22 (2013.01); C08K 5/57 (2013.01); C08L 2203/10 (2013.01); C08L 2203/18 (2013.01)

(58) Field of Classification Search
USPC ......................................................... 528/307
See application file for complete search history.

(56) References Cited

PUBLICATIONS

Yong-MeiRen, et.al. Divaccinosides A-D, four rare iridoid glucosidic truxillate esters from the leaves of Vaccinium bracteatum Author links open overlay panel Tetrahedron Letters,vol. 58, Issue 24, Jun. 14, 2017, pp. 2385-238 (Year: 2017).*
Rahul K. Shahni,Synthesis and characterization of BPA-free polyesters by incorporating a semi-rigid cyclobutanediol monomer; Journal of Polymer Chemistry; Issue 37, 2020 (Year: 2020).*

* cited by examiner

*Primary Examiner* — Terressa Boykin
(74) *Attorney, Agent, or Firm* — Kinney & Lange, P. A.

(57) ABSTRACT

A polymer includes a plurality of repeated polymerized units according to scheme (2):

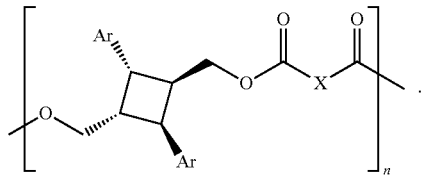

14 Claims, 11 Drawing Sheets

POLYMERS COMPRISING 1,3-CYCLOBUTANE DIMETHANOL (CBDO-1)

CROSS-REFERENCE TO RELATED APPLICATION(S)

This application is a continuation-in-part of U.S. application Ser. No. 16/934,390 filed Jul. 21, 2020 for "POLYMERS COMPRISING 1,3-CYCLOBUTANE DIMETHANOL (CBDO-1)" by Qianli Chu and Rahul Shahni, the disclosure of which is herein incorporated by reference in its entirety. To the extent any inconsistency may be found between this disclosure and the earlier filed application incorporated by reference, this disclosure will prevail.

STATEMENT OF GOVERNMENT INTEREST

This invention was made with government support under Grant No. 1355466 awarded by the National Science Foundation. The government has certain rights in the invention.

BACKGROUND

Synthetic polymers have become a prime material of choice around the globe because of their diverse applications. Among these, Bisphenol A (BPA) is an organic synthetic compound with the chemical formula $(CH_3)_2C(C_6H_4OH)_2$ and is a precursor to important plastics, primarily certain polycarbonates and epoxy resins, as well as some polysulfones. For example, BPA-based polycarbonates and epoxy resins exhibit exceptional thermal, mechanical, and optical properties, making them perfect for durable goods and engineering applications. BPA polymers' success is evidenced by their considerable market consumption. In 2015, an estimated 4 million tons of BPA-derived chemicals were produced worldwide and used to make consumer goods such as plastic bottles including water bottles, food storage containers, baby bottles, sports equipment, CDs, and DVDs. Epoxy resins derived from BPA are used to line water pipes, as coatings on the inside of many food and beverage cans and in making thermal paper such as that used in sales receipts.

However, the use of BPA-based chemicals has come under scrutiny due to the potential carcinogenic and disruptive endocrine effects of BPA. Several governments have investigated its safety, which prompted some retailers to withdraw polycarbonate products. As such, it is desirable to find alternative polymers with similar thermal, mechanical, and optical properties for replacement of BPA.

SUMMARY

A polymer includes a plurality of repeated polymerized units according to scheme (2):

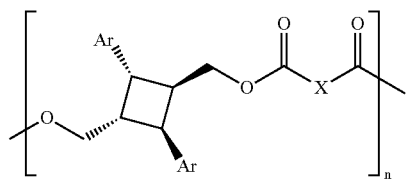

A method of making a polymer includes dimerizing trans-cinnamic acid, forming CBDA-1 and reducing CBDA-1, forming CBDO-1. The method includes condensing CBDO-1 with a diacid, forming monomeric subunits and polymerizing the monomeric subunits together to form the polymer.

DETAILED DESCRIPTION

Figure 1:
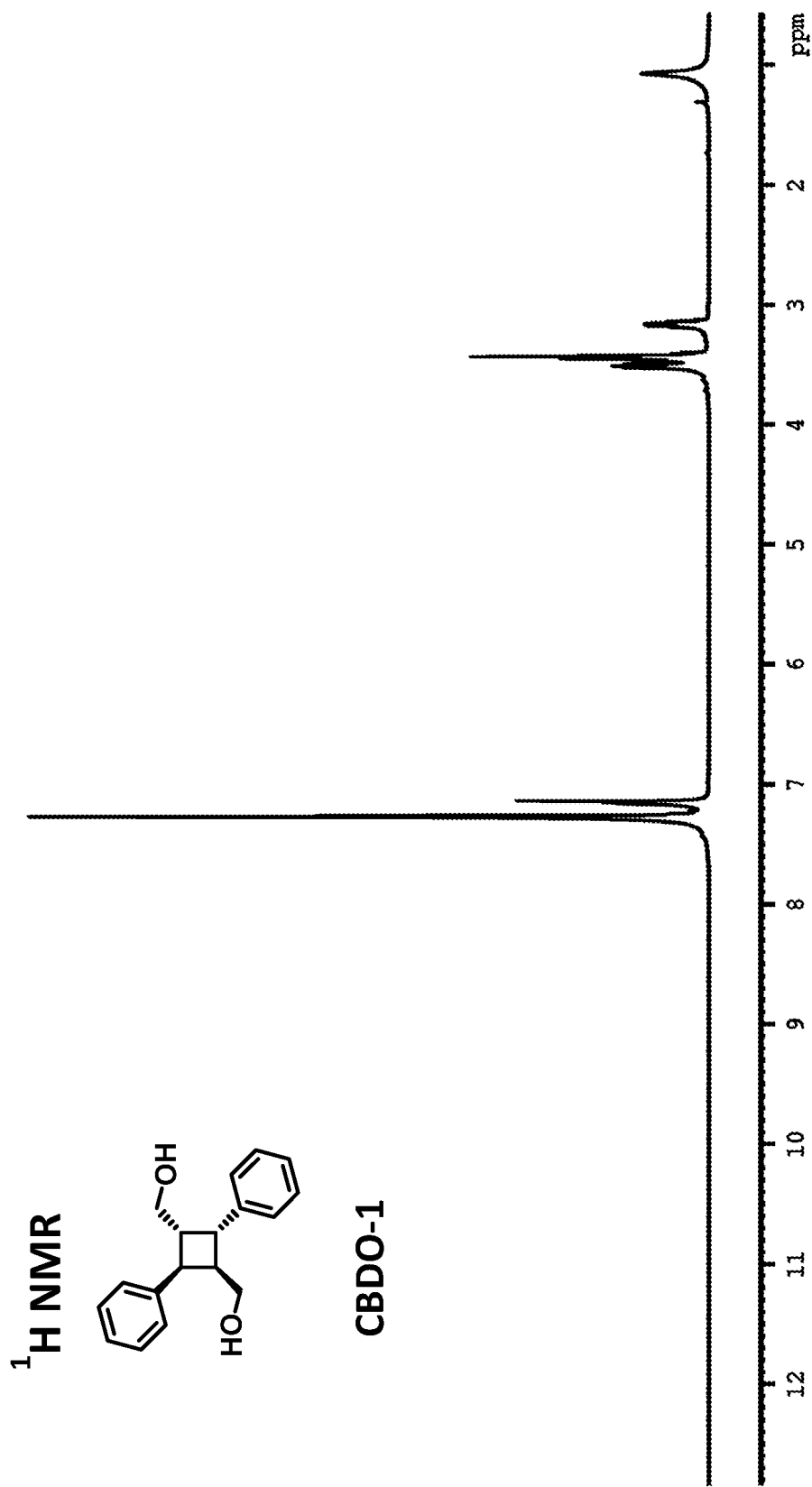
FIG. 1 is a $^1$H NMR spectrum of CBDO-1.

Disclosed, herein, is a strategy to synthesize a semi-rigid diol, trans 1,3-cyclobutane dimethanol (CBDO-1), which presents a versatile building block for forming a new class of polymers that may serve as phenol-free BPA replacements.

Limited success has been made in developing conventional polymers with thermal and mechanical properties similar to BPA-derived polymers by incorporating semi-rigid cyclic monomers, such as octahydro-2,5-pentalenediol and isohexides into the polymer structure. For example, 1,4-cyclohexane dimethanol (CHDM) and 2,2,4,4-tetramethyl-1,3-cyclobutanediol (TMCD) have achieved some commercial success and have been used in a variety of polyester and co-polyester products, including BPA-free water and baby bottles. However, the ability to introduce functional groups onto the cyclobutane ring of TMCD to tune the properties of the corresponding polymers is inherently limited because TMCD is mainly produced through flash vacuum pyrolysis (FVP). Furthermore, the high melting point and low reactivity of TMCD makes it difficult to manufacture high molecular weight polymers. As such, only 25 mol % of TMCD is conventionally used to synthesize copolymers.

CBDO-1 has two rigid phenyl rings that give CBDO-1 desirable thermal, mechanical, and optical properties similar to BPA but, unlike BPA, CBDO-1 does not have a phenol group, which is thought to enable BPA to trigger estrogenic pathways in the body. Furthermore, CBDO-1 is more reactive than TMCD, offering more flexibility to introduce functional groups and manufacture higher molecular weight polymers. As such, CBDO-1 may serve as a BPA replacement with reduced carcinogenic and disruptive endocrine effects.

The cyclobutane-comprising polymers (CBPs) synthesized using CBDO-1 have high thermal stability. The incorporation of the semi-rigid CBDO-1 moiety in a polyester was able to increase the glass transition temperature by 30° C. or more even at low molecular weights. For example, the $T_g$s of PCBS, PCBA, PCBT, and PCBF were 30-80° C. higher than commercially available polyethylene succinate, polyethylene adipate, PET (polyethylene terephthalate) and PEF (polyethylene 2,5-furandicarboxylate), respectively.

CBDO-1 can be synthesized from trans-cinnamic acid using, for example, a solid-state approach or a brine slurry approach. Solid trans-cinnamic acid can be placed on a surface or suspended in liquid and exposed to UV radiation, forming rctt-2,4-diphenylcyclobutane-1,3-dicarboxylic acid (CBDA-1) through a [2+2] photocycloaddition reaction, which is the combination of an excited state alkene with a ground state alkene to produce a cyclobutane. Factors such as, for example, increasing the surface area of the trans-cinnamic acid exposed to UV radiation, can increase the rate of reaction and result in a yield of 95% or more conversion of trans-cinnamic acid to CBDA-1.

CBDA-1 can be converted to CBDO-1 by using a suitable reducing agent such as, for example, sodium borohydride ($NaBH_4$) in the presence of iodine ($I_2$) as an electrophile, or $LiAlH_4$ and a suitable solvent such as, for example, tetrahydrofuran (THF) or diethyl ether. CBDA-1 can also be converted to CBDO-1 by catalytic hydrogenation in the presence of zinc, copper, chromium, iron, nickel, cobalt, palladium, iridium, ruthenium, rhenium, molybdenum, platinum, or their corresponding oxides. CBDO-1 can be further purified by any technique known in the art such as recrystallization. In one embodiment, CBDO-1 synthesis from trans-cinnamic acid can be summarized by reaction Scheme 1:

Scheme 1. Synthesis of CBDO-1 from trans-cinnamic acid.

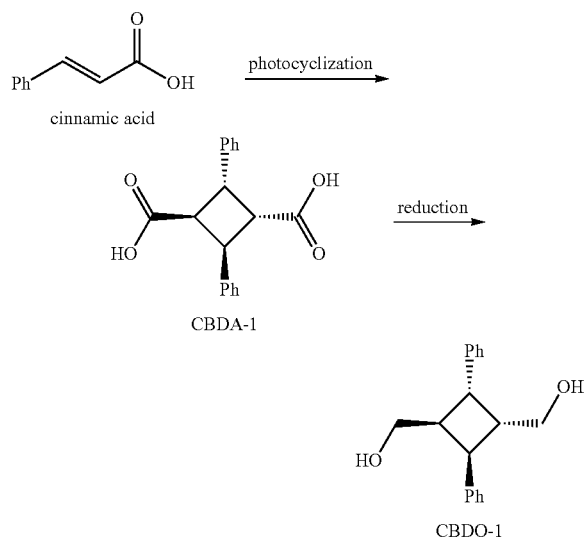

The CBDO-1 chemical structure was confirmed by HRMS, FT-IR, $^1H$ and $^{13}C$ NMR, and single crystal X-ray diffraction.

CBDO-1 can be used as a versatile monomer to form a variety of polyesters using a two-step polycondensation reactions with a catalyst such as, for example, metal oxides, salts of silicon, aluminum, zinc, lead, zirconium, antimony, cobalt, or alkoxide, organometallic compounds of tin, lead, titanium, or tetravalent hafnium compounds. In one embodiment, the polycondensation reaction can be carried out using an aliphatic diacid or aromatic diacid such as, for example, oxalic acid, malonic acid, succinic acid, glutaric acid, adipic acid, terephthalic acid, 2,5-furandicarboxylic acid, and CBDA-1. The polycondensation reaction forms the corresponding CBP such as, for example, polycyclobutane oxalate (PCBO), polycyclobutane malonate (PCBM), polycyclobutane succinate (PCBS), polycyclobutane glutarate (PCBG), polycyclobutane adipate (PCBA), polycyclobutane terephthalate (PCBT), polycyclobutane furandicarboxylate (PCBF), and polycyclobutane-1,3-cyclobutane-dicarboxylate (PCBC). In one embodiment, the polycondensation reaction can be summarized by the following reaction Scheme 2:

Scheme 2. Synthesis of CBDO-1 based polyesters.

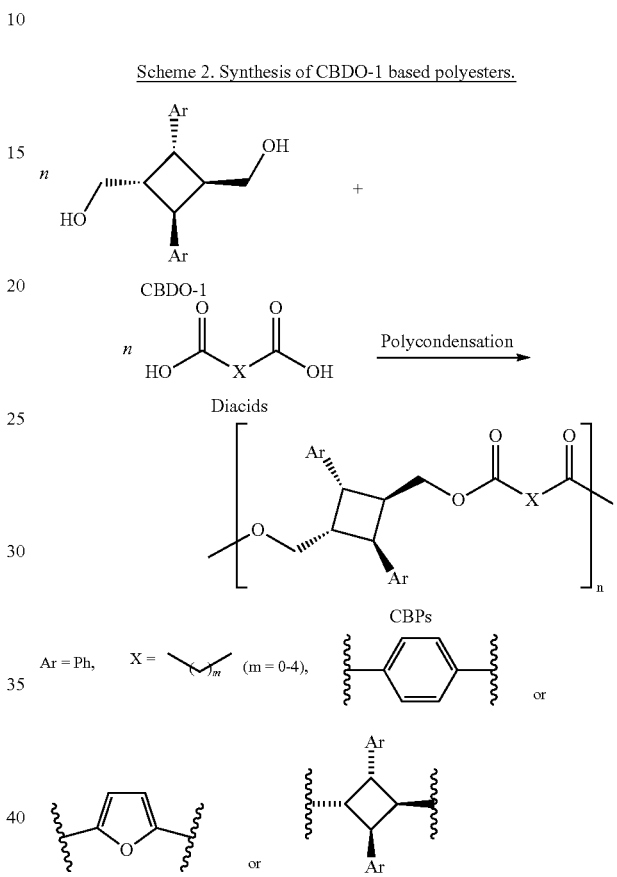

In one embodiment, X has less than 20 carbons and can be, for example, a diacid with an aliphatic chain, an aliphatic heterochain, a branched aliphatic chain, an aliphatic ring, an aromatic ring, or a heterocyclic ring.

In one embodiment, Ar is a non-substituted aromatic ring and can be, for example, benzene, furan, thiophene, or pyridine.

In one embodiment, Ar is a substituted aromatic ring. The substituents can be, for example, methanyl, methoxyl, hydroxyl, or halogens.

Example 1

Solvent-free dimerization of trans-cinnamic acid was performed using residential blacklights. Three 15 W Eiko EK15526 F15T8/BL bulbs were placed about 1.5 cm above an 8×4 inch glass plate with 2.00 g of uniformly dispersed trans-cinnamic acid powder on the glass plate, and three bulbs were placed about 1.5 cm below the glass plate. The powder was periodically re-blended uniformly to ensure even irradiation. After a total of about 60 hours, the powder was collected and washed with 3 mL ethanol to obtain the product, rctt-2,4-diphenylcyclobutane-1,3-dicarboxylic acid, CBDA-1, as a white solid (1.94 g, 97% yield).

Example 2

The dimerization of trans-cinnamic acid was also carried out in slurry conditions. Specifically, 5.00 g trans-cinnamic acid powder was suspended in 2 L of brine solution in a crystallizing dish or beaker with magnetic stirring. Three E27 40 W HD 159 black lights were immersed in the crystallizing dish and the slurry was continuously stirred for 72 hours. The slurry was filtered, and the solid was washed with 10 mL ice-cold water. After air drying, the desired product, CBDA-1, was obtained as a white solid (4.75 g, 95% yield).

Although the dimerization of trans-cinnamic acid was also carried out in water, only a yield of 78% (3.9 g) was achieved mainly due to the solubility of trans-cinnamic acid in water compared to a brine solution. In water, trans-cinnamic acid tended to agglomerate on the surface of the glassware, slowing down the reaction and making it difficult to collect the final product compared to the brine solution.

Example 3

CBDA-1 from Examples 1 and 2 was reduced and formed CBDO-1. Specifically, in a 100 mL round bottom flask fitted with a Claisen head adaptor, a magnetic stir bar and fine powered $NaBH_4$ (1.28 g, 33.75 mmol—8 molar equivalents) was added to 25 mL of THF. This suspension was stirred for 10 min, and then CBDA-1 (1.00 g, 3.37 mmol) was added to the suspension. The addition resulted in bubbling. When the reaction mixture stopped bubbling, a solution of $I_2$ (2.14 g, 8.44 mmol) in THF (15 mL) was added dropwise, using a dropping funnel attached to the Claisen head, over a period of 45-60 min. The addition of $I_2$ is an exothermic reaction and resulted in significant evolution of $H_2$ gas. During this addition, the color of the mixture changed from red to yellow to colorless, indicating the disappearance of $I_2$.

After the disappearance of all $I_2$, a water condenser was attached to the Claisen head, and the solution was heated to reflux. After 16 hours of refluxing, the reaction mixture was analyzed using TLC (10% Methanol in Dichloromethane as solvent) to verify the absence of the starting material, CBDA-1. Approximately 40 mL of THF was removed using the rotavapor and a white solid was collected from the flask. To this white solid, 20 mL of cyclohexane and 30 mL of 10% NaOH was added and stirred until bubbling from the mixture ceased (approximately 30 min). After 1 hour a white solid separated out of the solution. The white solid was filtered using Buchner funnel and washed 3 times with 10 mL of 3M $NH_4OH$, followed by 10 mL of 12% $NaHSO_3$ to remove any residual $I_2$. The white solid obtained after filtration was dissolved in chloroform and washed 3 times with saturated brine solution. The removal of chloroform yielded the desired product CBDO-1 (0.84 g; 93% yield) as a white solid.

In other embodiments, reduction can be achieved using boranes. For example, CBDA-1 (1.00 g, 3.72 mmol) was added to THF (20.1 mL) under an atmosphere of nitrogen and cooled to 0° C. $BH_3 \cdot THF$ (1 M solution in THF, 11.17 mL) was then added to the reaction over 15 min to maintain the temperature below 10° C. The reaction was stirred for 14 hours. The reaction mixture was analyzed using TLC to verify the absence of starting material. Approximately 40 mL of THF was removed using the rotavapor and a white solid was collected from the flask. 20 mL of cyclohexane and 30 mL of 10% NaOH was then added and stirred until bubbling from the mixture ceased (approximately 30 min). After 1 hour a white solid separated out of the solution. The white solid was filtered using a Buchner funnel, dissolved in chloroform, and washed 3 times with saturated brine solution.

In one embodiment, catalytic hydrogenation was carried out in a 40 ml pressurized reactor equipped with a mechanical stirrer, thermocouple, and a liquid sample line loaded with CBDA-1 (0.5 g, 1.86 mmol), the CuO $Cr_2O_3$ catalyst (0.1 g), and 1,4 dioxane (25 mL). The reactor was purged with $N_2$ gas to remove air, and then pressurized to 4 MPa using $H_2$. After heating the reactor to 240° C., the $H_2$ pressure was increased to 8 MPa. The mixture was stirred at 500 rpm for 12 hours and the reaction product was analyzed by GC.

CBDO-1 molecular and structural confirmation was obtained from high resolution mass spectrometry (ESI/TOF), NMR and FT-IR spectroscopy, X-ray crystal diffraction, and melting point determination. Three concordant melting point readings were taken: 1) 106.5-106.9° C.; 2) 106.4-107.0° C.; and 3) 106.4-107.0° C.

Selected single crystal X-ray diffraction data of CBDO-1 are reported in Table 1.

TABLE 1

X-ray crystal diffraction data of CBDO-1.

| CBDO-1 | Data |
|---|---|
| CCDC # | 1949075 |
| Formula | C36 H40 O4 |
| FW | 536.68 |
| Crystal Size [mm] | 0.06 × 0.121 × 0.375 |
| Crystal_system | orthorhombic |
| Space Group, Z | Pna2$_1$ |
| a (Å) | 17.9616 (7) |
| b (Å) | 7.6761 (3) |
| c (Å) | 21.5205(9) |
| α (°) | 90 |
| β (°) | 90 |
| γ (°) | 90 |
| V (Å3) | 2967.1(2) |
| Temp. (K) | 110(2) |
| pcalc [g/cm$^3$] | 1.201 |
| μ [mm$^{-1}$] | 0.604 |
| Radiation Type | CuK\a |
| F(000) | 1152 |
| No of measured refl. | 73145 |
| of independent refl. | 5263 |
| No of refl. (I ≥ 2σ) | 4930 |
| R1/wR2 (I ≥ 2σ) [%] | 7.82/20.40 |
| R1/wR2 (all data) [%] | 8.25/20.71 |

Rhombic crystals of CBDO-1 were obtained from ethyl acetate and hexane (3:1) solution by slow evaporation at room temperature. Single crystal X-ray diffraction was used to elucidate the structure of CBDO-1. The crystal structure revealed that the two methanol groups are on the 1 and 3 positions of the cyclobutane ring and are trans to each other, which is the same configuration as their parent carboxylic acid groups in the starting material of CBDA-1. The space group is Pna21 and there are two molecules in each asymmetric unit cell. The two cyclobutane rings in each asymmetric unit adopt 18.61° and 22.02° puckered conformations. The angles in the cyclobutane ring are 89.00, 88.55, 90.06, and 88.13 degrees, which indicate ring strain in the structure. Each hydroxyl group forms two hydrogen bonds with the two hydroxyl groups of the two neighboring molecules to form a supramolecular helix, which plays an important role in determining the melting point of CBDO-1

(106.4-107.0° C.). For comparison, the melting point of its diacid parent molecule, CBDA-1, is about 175° C. higher. The distance between oxygen atoms in the four hydrogen bonds is 2.734, 2.758, 2.764, and 2.769 A°, respectively. Although the hydrogen-bonded helix is chiral, each crystal is racemic. CBDO-1 is soluble in organic solvents such as, for example, acetone, ethyl acetate, diethyl ether, and chloroform.

The high-resolution mass spectrum of CBDO-1 has an experimental mass/z of 291.1370 for CBDO-1, which is within the margin of error of the calculated mass/z of 291.1361.

The FT-IR spectrum of CBDO-1 has primary peaks at (v)=3307.12, 2931.36, 1448.66, 1496.15, 1014.64, 1600.72, 743.33, and 696.68 $cm^{-1}$.

FIG. 1 is a $^1H$ NMR spectrum of CBDO-1. FIG. 1 shows the 500 MHz spectrum of CBDO-1 in $CDCl_3$: δ=1.07 (s, 2H), 3.12-3.18 (m, 2H), 3.40-3.47 (m, 4H) 3.49-3.52 (m, 2H), and 7.13-7.27 (m, 12H) ppm.

A $^{13}C$ NMR spectrum of CBDO-1 was obtained at 125 MHz in $CDCl_3$: δ 36.37, 37.64. 58.45, 121.80, 122.90, 123.87, and 134.92 ppm.

Examples 4-10

Polycondensation reactions were conducted in a 15 mL round bottom flask containing a magnetic stir bar and equipped with a Claisen head, one neck being attached to an Argon gas inlet and the other neck connected to a water condenser. A finely grounded mixture of CBDO-1 (1.06 mmol) and a dicarboxylic acid (1.28 mmol) was charged in the reaction flask. The dicarboxylic acid was selected from the group consisting of oxalic acid, malonic acid, succinic acid, glutaric acid, adipic acid, terephthalic acid, 2,5-furandicarboxylic acid, and CBDA-1. The reaction mixture was placed under vacuum and purged with argon gas—evacuating and purging with argon gas was repeated three times. The method of polycondensation involved two steps. In the first step, the reaction was carried out under argon gas to promote the formation of oligomers.

The reaction mixture was heated in the sand bath at 130° C. for 15 min with constant stirring. When complete melting of the mixture was observed, the catalyst, titanium isopropoxide $Ti(OCH(CH_3)_2)_4$ (1.25 mol %), in 1 mL of toluene, was added to the reaction flask under continuous flow of argon gas. Afterwards, the temperature was increased to 170° C. and allowed to stir for 12 hours, and finally to 200-215° C. for 1.5 hours to complete the first step.

The condensation reaction is performed solvent-free. A small amount of toluene (1 ml) was added to form an azeotropic mixture with the water formed from the condensation reaction. The azeotropic mixture was readily removed from the reaction mixture at high temperatures to avoid deactivation of the titanium catalyst.

In the second step of polycondensation, the oligomers were connected forming a long chain. A vacuum was gradually applied to the reaction step at 210-215° C. for 2 hours. After reaction completion, the reaction mixture was cooled to room temperature under the flow of argon gas. The polymer was further purified by dissolving it in 5 mL of a chloroform-TFA mixture (6:1). The polymer was then precipitated by adding 50 mL of methanol, subsequently filtered, and then dried in vacuum at 40° C. for 12 hours. All the polyesters precipitated as amorphous powders with isolated yields of 72-87%. Each polymer was substantially formed only of the corresponding monomeric subunit. In other words, substantially no partial monomeric subunits were incorporated into the polymer backbone such as, CBDO-1 without the diacid or the diacid without CBDO-1.

Each of the polymers, polycyclobutane oxalate (PCBO), polycyclobutane malonate (PCBM), polycyclobutane succinate (PCBS), polycyclobutane glutarate (PCBG), polycyclobutane adipate (PCBA), polycyclobutane terephthalate (PCBT), polycyclobutane furandicarboxylate (PCBF), and polycyclobutane-1,3-cyclobutane-dicarboxylate (PCBC) were synthesized from their corresponding diacids. The polymers can also be synthesized from the polycondensation between CBDO-1 and the corresponding diesters, such as methyl diesters, of the diacid. The polymers were confirmed by FT-IR and NMR.

Figure 2:
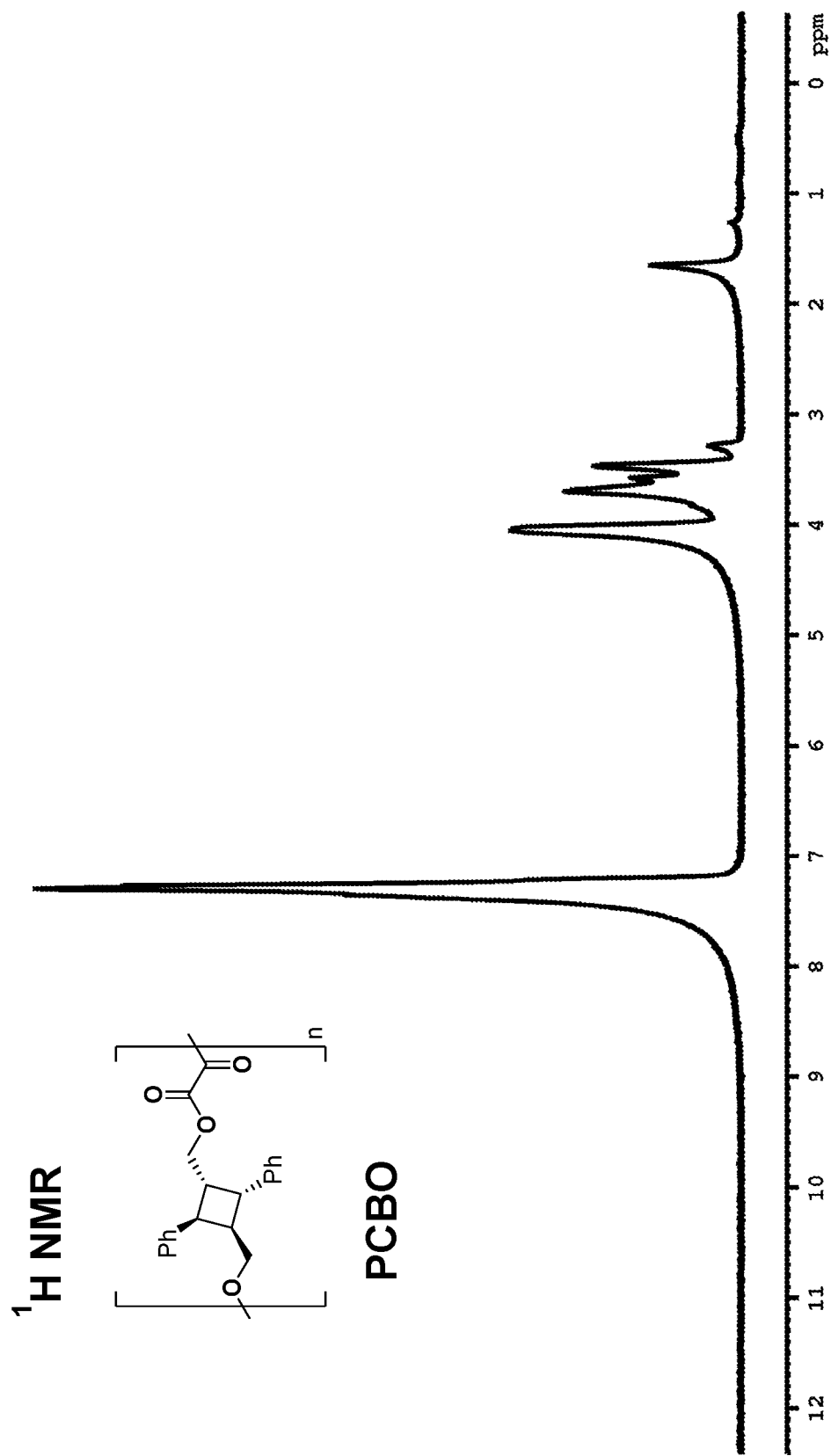
FIG. 2 is a $^1$H NMR spectrum of PCBO.

FIG. 2 is a $^1H$ NMR spectrum of PCBO in $CDCl_3$ at room temperature. FIG. 2 shows the 500 MHz spectrum of PCBO in $CDCl_3$: δ=3.29-3.72 (m, 2H), 4.05 (s, 2H), 7.30 (s, 5H) ppm.

A $^{13}C$ NMR spectrum of PCBO at room temperature was obtained at 125 MHz in $CDCl_3$: δ=39.10, 41.86, 63.44, 67.07, 127.41, 128.09, 128.33, 129.04, 129.21 ppm.

The FT-IR spectrum of PCBO has primary peaks at (v)=3026.52, 2938.94, 1740.28, 1234.35, 1080.48 $cm^{-1}$.

Figure 3:
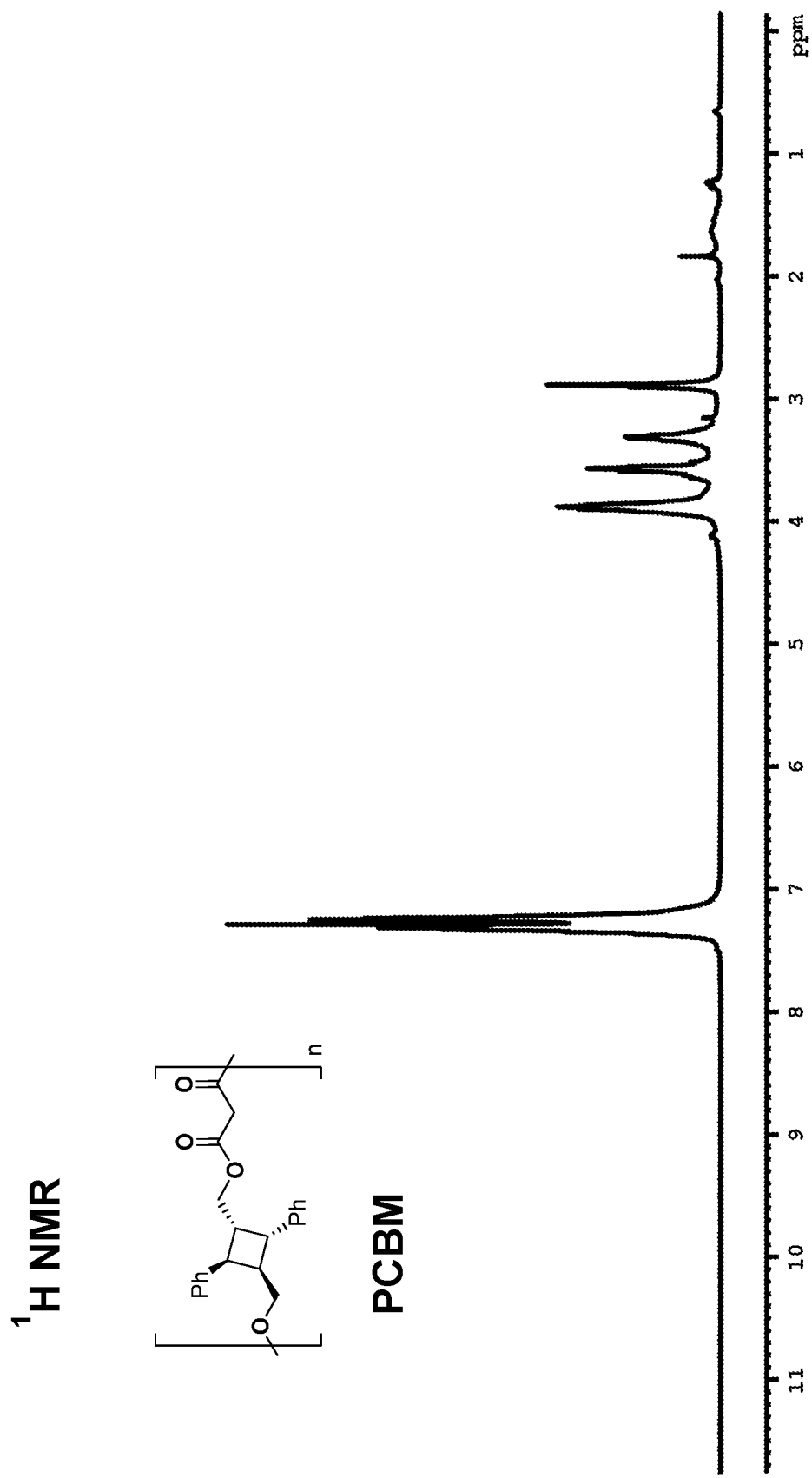
FIG. 3 is a $^1$H NMR spectrum of PCBM.

FIG. 3 is a $^1H$ NMR spectrum of PCBM in $CDCl_3$ at room temperature. FIG. 3 shows the 500 MHz spectrum of PCBM in $CDCl_3$: δ=2.91 (s, 2H), 3.34 (s, 2H), 3.58 (s, 2H), 3.90 (s, 2H), 7.23-7.31 (m, 10H) ppm.

A $^{13}C$ NMR spectrum of PCBM at room temperature was obtained at 125 MHz in $CDCl_3$: δ=39.14, 41.31, 42.03, 66.01, 127.18, 128.08, 128.92, 138.93, 166.37 ppm.

The FT-IR spectrum of PCBM has primary peaks at (v)=2944.19, 1728.12, 1143.08, 1004.63 $cm^{-1}$.

Figure 4:
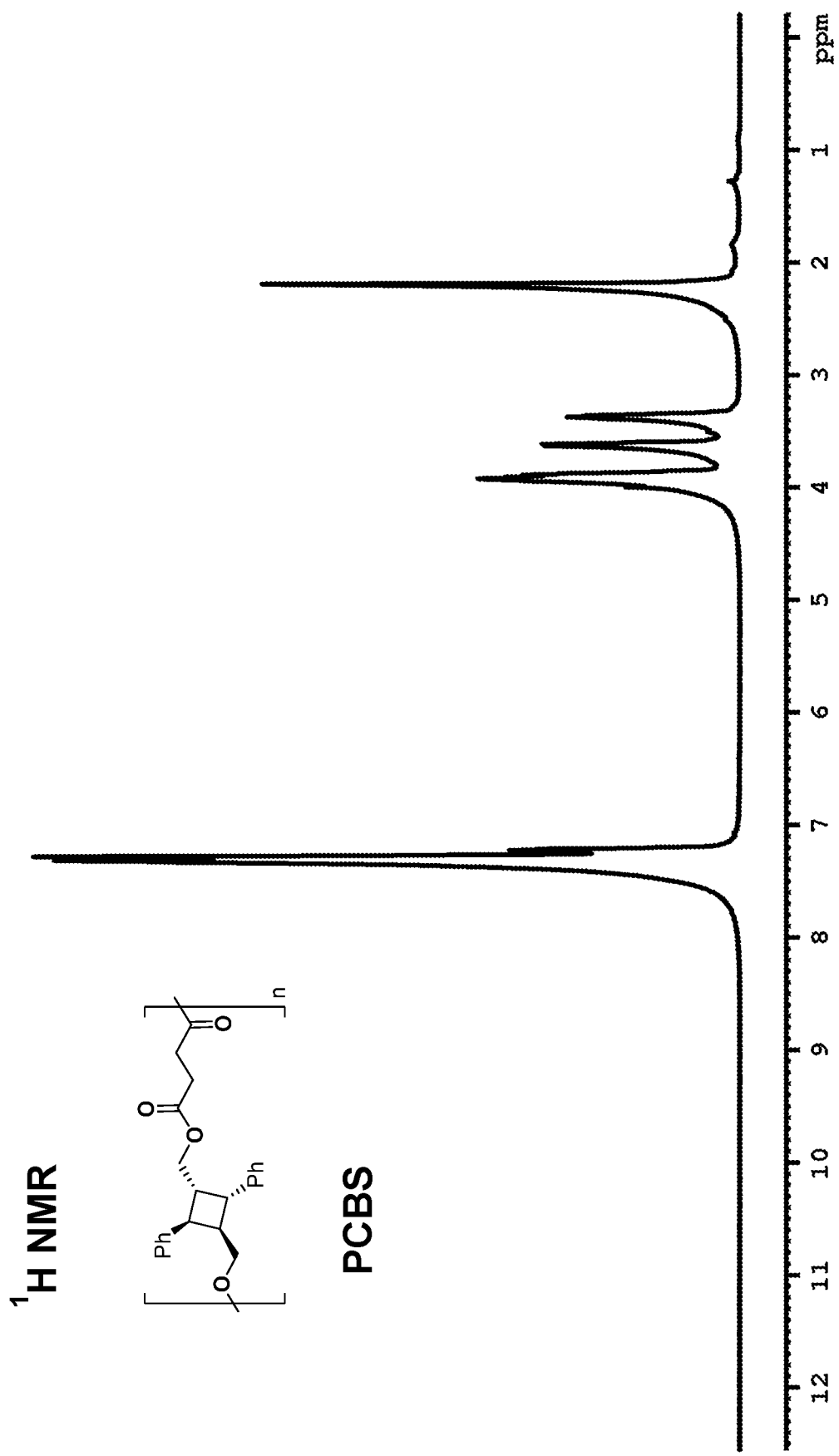
FIG. 4 is a $^1$H NMR spectrum of PCBS.

FIG. 4 is a $^1H$ NMR spectrum of PCBS in $CDCl_3$ at room temperature. FIG. 4 shows the 500 MHz spectrum of PCBS in $CDCl_3$: δ=2.20 (s, 2H), 3.37 (s, 1H), 3.63 (s, 1H), 3.93 (m, 2H) 7.23-7.32 (m, 5H) ppm.

A $^{13}C$ NMR spectrum of PCBS at room temperature was obtained at 125 MHz in $CDCl_3$: δ=29.05, 39.38, 42.09, 65.25, 127.08, 128.13, 128.87, 139.20, 172.30 ppm.

The FT-IR spectrum of PCBS has primary peaks at (v)=2924.51, 1728, 1150.50 $cm^{-1}$.

Figure 5:
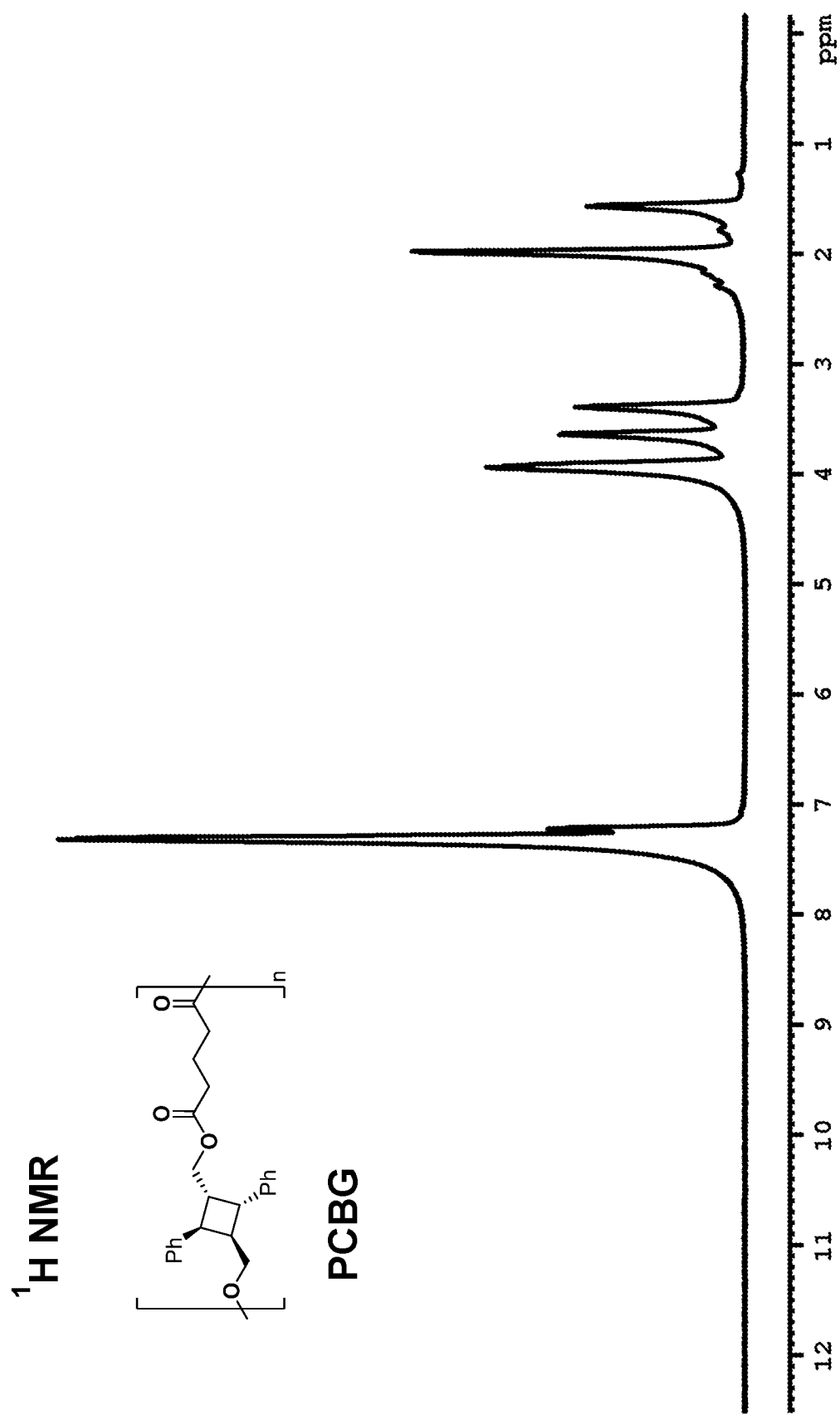
FIG. 5 is a $^1$H NMR spectrum of PCBG.

FIG. 5 is a $^1H$ NMR spectrum of PCBG in $CDCl_3$ at room temperature. FIG. 5 shows the 500 MHz spectrum of PCBG in $CDCl_3$: δ=1.57 (s, 1H), 1.98 (s, 2H), 3.39 (s, 1H), 3.64 (s, 1H), 3.94 (s, 2H), 7.22-7.32 (m, 5H) ppm.

A $^{13}C$ NMR spectrum of PCBG at room temperature was obtained at 125 MHz in $CDCl_3$: δ=20.10, 33.31, 39.57, 42.21, 65.01, 127.09, 128.24, 128.87, 139.27, 173.03 ppm.

The FT-IR spectrum of PCBG has primary peaks at (v)=2942.10, 1727.41, 1147.00 $cm^{-1}$.

Figure 6:
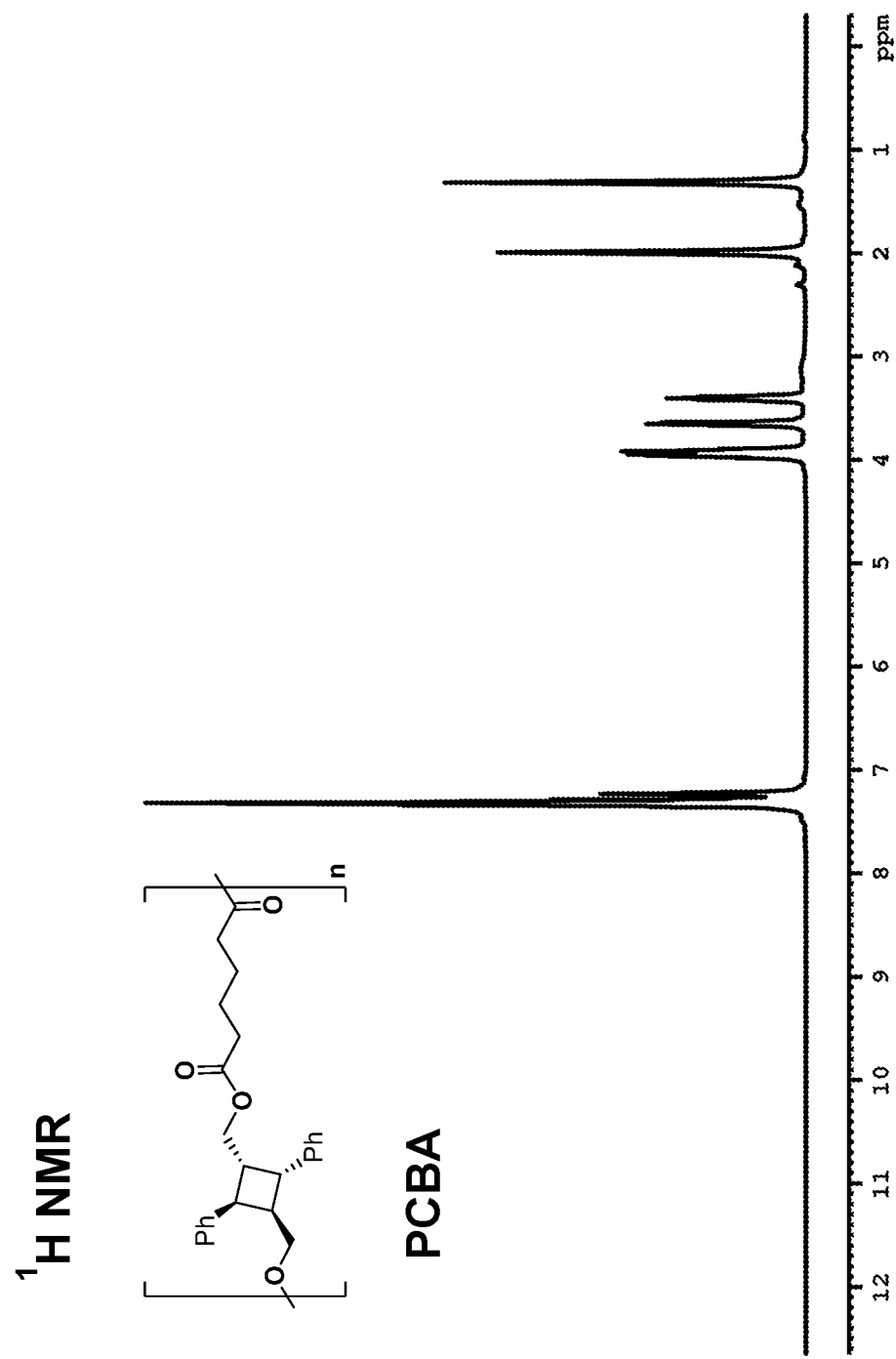
FIG. 6 is a $^1$H NMR spectrum of PCBA.

FIG. 6 is a $^1H$ NMR spectrum of PCBA in $CDCl_3$ at room temperature. FIG. 6 shows the 500 MHz spectrum of PCBA in $CDCl_3$: δ=1.34 (s, 2H), 2.02 (s, 2H), 3.43 (t, 1H), 3.67 (t, 1H), 3.94 (m, 2H), 7.23-7.32 (m, 5H) ppm.

A $^{13}C$ NMR spectrum of PCBA at room temperature was obtained at 125 MHz in $CDCl_3$: δ=24.44, 33.94, 39.52, 42.19, 64.98, 127.07, 128.86, 139.31, 173.46 ppm.

The FT-IR spectrum of PCBA has primary peaks at (v)=2942.45, 1727.52, 1139.05 $cm^{-1}$.

Figure 7:
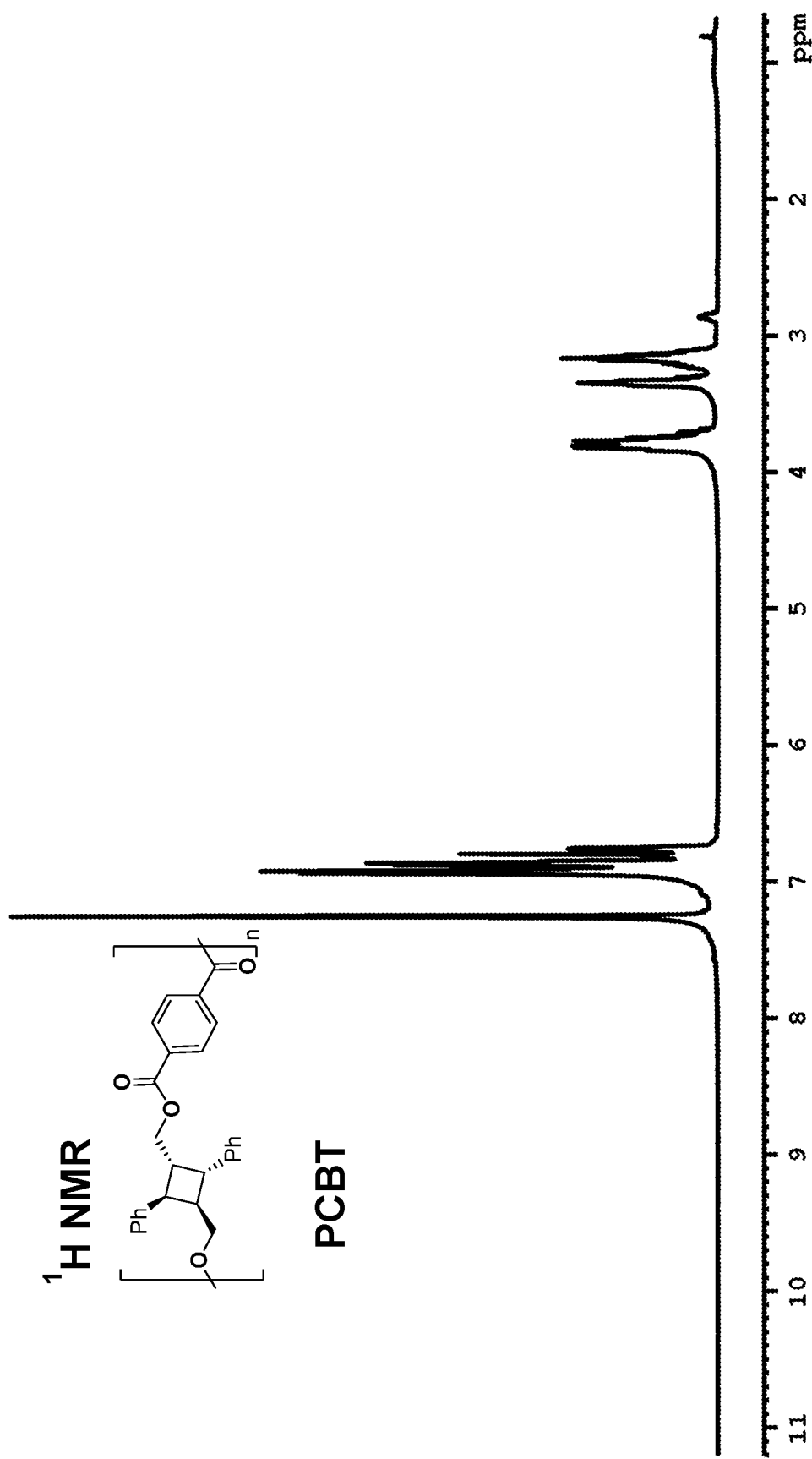
FIG. 7 is a $^1$H NMR spectrum of PCBT.

FIG. 7 is a $^1H$ NMR spectrum of PCBT in $CDCl_3$ at room temperature. FIG. 7 shows the 500 MHz spectrum of PCBT in $CDCl_3$:=3.16 (m, 1H), 3.35 (s, 1H), 3.80 (m, 2H), 6.76-6.93 (m, 5H) ppm.

A $^{13}C$ NMR spectrum of PCBT at room temperature was obtained at 125 MHz in $CDCl_3$: δ=34.59, 37.04, 60.55, 121.96, 122.94, 123.76, 124.38, 128.74, 133.85, 160.56 ppm.

The FT-IR spectrum of PCBT has primary peaks at (v)=2941.32, 1708.74, 1264.18, 1100.43 cm$^{-1}$.

Figure 8:
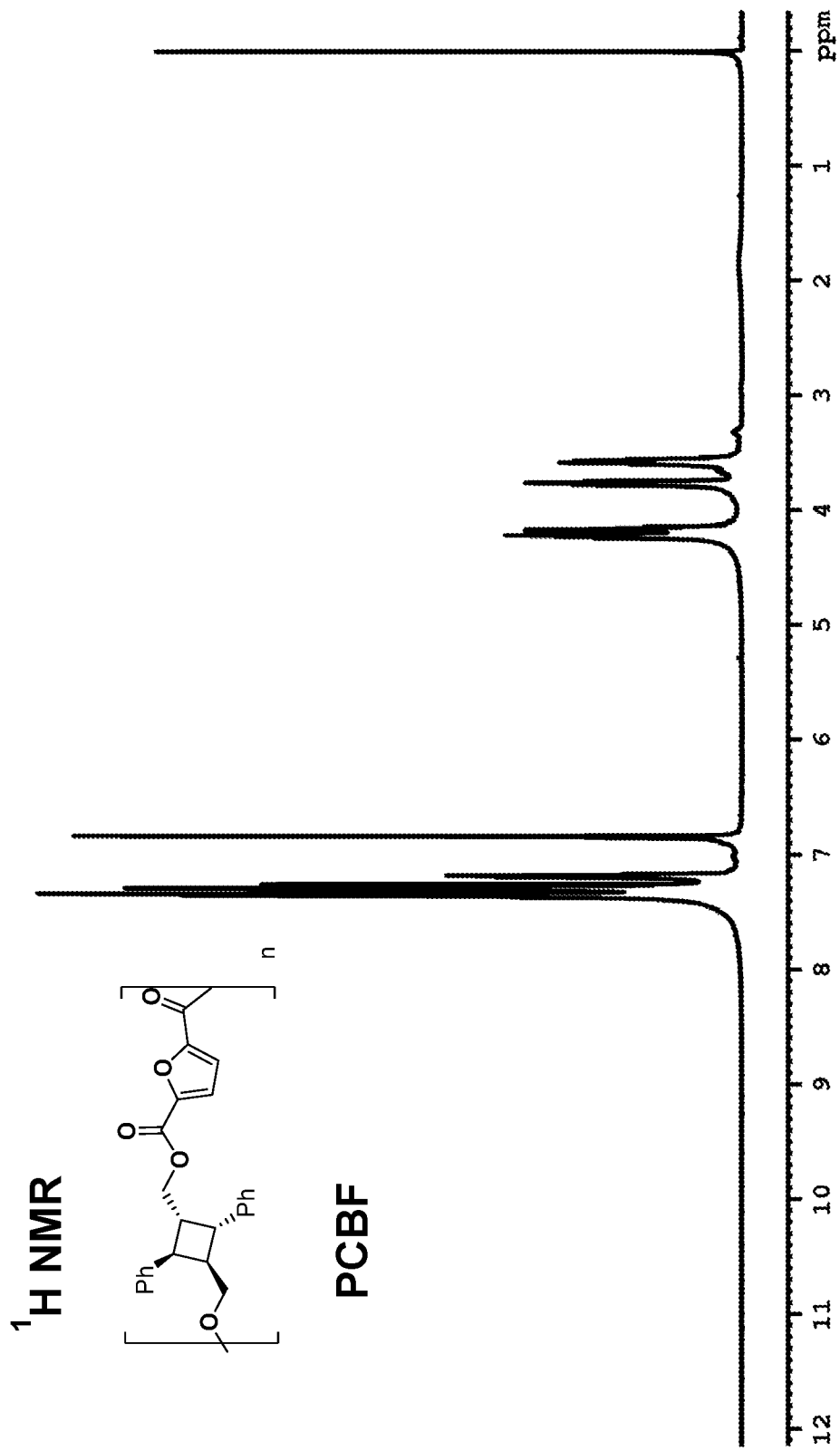
FIG. 8 is a $^1$H NMR spectrum of PCBF.

FIG. 8 is a $^1$H NMR spectrum of PCBF in CDCl$_3$ at room temperature. FIG. 8 shows the 500 MHz spectrum of PCBF in CDCl$_3$: δ=3.53-3.60 (m, 1H), 3.76 (t, 1H), 4.16-4.24 (m, 2H), 6.83 (s, 1H), 7.18 (t, 1H), 7.29 (t, 2H), 7.24 (d, 2H), ppm.

A $^{13}$C NMR spectrum of PCBF at room temperature was obtained at 125 MHz in CDCl$_3$: δ=39.20, 41.75, 65.45, 118.11, 126.81, 127.62, 127.79, 128.54, 138.43, 146.47, 157.53 ppm.

The FT-IR spectrum of PCBF has primary peaks at (v)=2942.85, 1716.13, 12.67.72, 1220.04, 1129.77 cm$^{-1}$.

Figure 9:
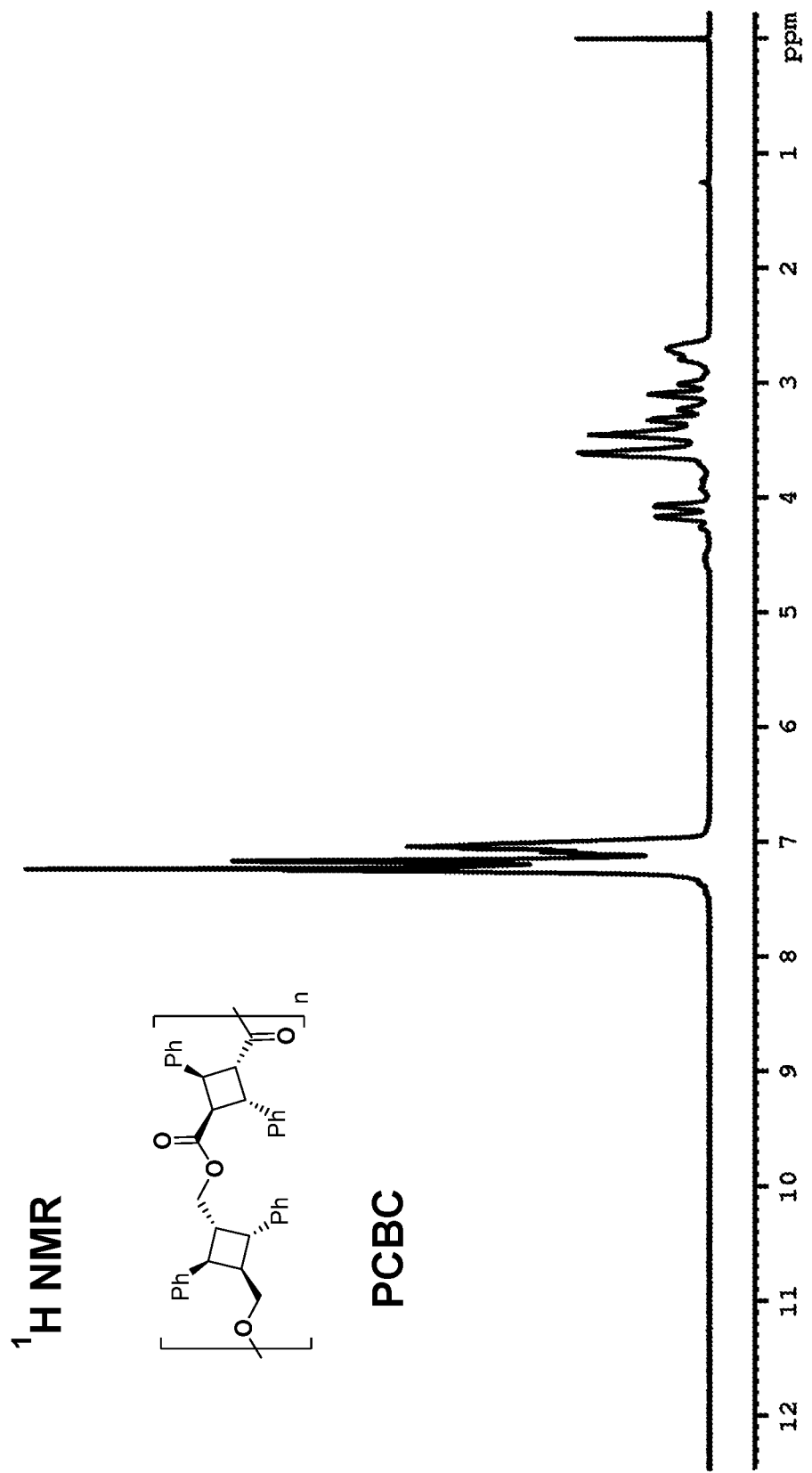
FIG. 9 is a $^1$H NMR spectrum of PCBC.

FIG. 9 is a $^1$H NMR spectrum of PCBC in CDCl$_3$ at room temperature. FIG. 9 shows the 500 MHz spectrum of PCBC in CDCl$_3$: δ=2.70-4.17 (m, 6H), 7.06 (t, 2H), 7.17-7.23 (m, 4H), ppm.

A $^{13}$C NMR spectrum of PCBC at room temperature was obtained at 125 MHz in CDCl$_3$: δ=39.29, 41.37, 41.97, 47.10, 64.74, 127.05, 127.41, 127.63, 127.92, 128.22, 128.81, 139.16, 139.24, 172.00 ppm.

The FT-IR spectrum of PCBC has primary peaks at (v)=3027.52, 1723.96, 1601.48, 1495.91, 1450.22, 1167.70, 744.67, 695.43 cm$^{-1}$.

As shown in Table 2, the molecular weight and molecular weight distribution of CBPs were measured by Gel Permeation Chromatography (GPC) and compared with the weight average molecular weight (Mw) data obtained from Diffusion Ordered NMR Spectroscopy (DOSY). DOSY linearly relates the chemical shifts of $^1$H NMR resonances to the translational diffusion coefficient of a particular molecular species, which could be applied to determine Mw of polymers in dilute solutions. In diluted conditions, viscosity and density remain consistent throughout the solution, hence the linear relation between Log Da and Log Mw using Stokes-Einstein equation. The commercial polystyrene (PS) standards were selected to obtain theD-Mw calibration curve due to its widespread use in GPC standards. Chloroform-d was used as a solvent due to its ability to dissolve most of the polyesters. The molecular weights of the CBPs can be increased by changing the reaction parameters such as, for example, increasing the reaction time or reducing the pressure used during the polymerization reaction.

TABLE 2

| CBP Samples | Molecular weight distribution (GPC) | | | Molecular weight data (DOSY$^a$) | |
|---|---|---|---|---|---|
| | $M_n$ g/mol | $M_w$ g/mol | PDI | $D_a$ m$^2$/s (10$^{-10}$) | $M_w$ g/mol |
| PCBA | 8,800 | 25,600 | 2.91 | 1.38 | 25,700 |
| PCBG | 5,300 | 8,900 | 1.66 | 2.33 | 9,500 |
| PCBM | 4,400 | 6,900 | 1.55 | 2.71 | 7,200 |
| PCBO | 6,300 | 14,900 | 2.28 | 1.79 | 15,700 |
| PCBS | 12,100 | 26,800 | 2.21 | 1.33 | 27,100 |
| PCBT | 11,000 | 23,100 | 2.11 | 1.48 | 22,300 |
| PCBF | 3,600 | 6,900 | 1.89 | 2.66 | 7,500 |
| PCBC | 23,400 | 34,900 | 1.49 | 1.15 | 35.600 |

$^a$M$_w$ (DOSY) was calculated from the calibration curve using the experimental values of D$_a$ of the synthesized CBPs.

Diffusion coefficients of the CBPs samples were fitted to the PS calibration curve to calculate the Mw. As shown in Table 2, the Mw of CBPs obtained from DOSY ranged between 7200 and 35,600, which were consistent with the results from GPC (6900-34,900).

Figure 10:
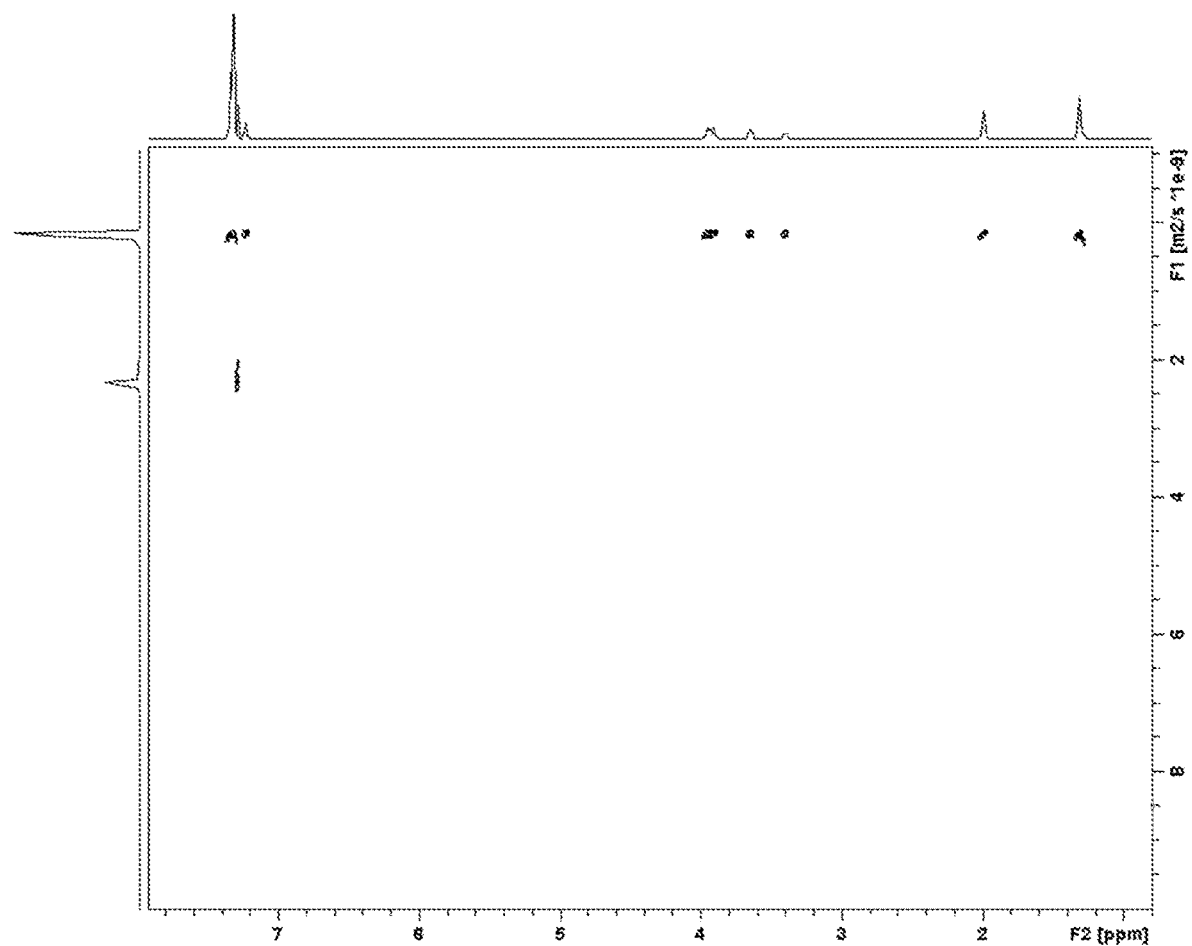
FIG. 10 is a DOSY spectrum of PCBA.

FIG. 10 is a DOSY spectrum of PCBA. FIG. 10 shows the 2D DOSY spectrum of PCBA in CDCl$_3$. Similar spectra were obtained for all the CBP samples.

A decay curve of cyclobutane ring protons from the PCBA DOSY spectrum has a chemical shift=3.67 ppm derived from DOSY on a PCBA sample using diffusion time Δ=100 ms. The data was fitted (−) with the Stejskal-Tanner equation (I=I$_o$exp−(γ$^2$G$^2$δ$^2$)D(Δ−δ/3)) to derive a diffusion coefficient D=1.375·10$^{-11}$, which using the PS calibration resulted in an Mw=25,700 g/mol. Similar decay curves were derived for all the CBP samples.

In one embodiment, PCBA has a molecular weight from 20,000 to 30,000 g/mol. In one embodiment, PCBA has a molecular weight from 10,000 to 50,000 g/mol. In some embodiments, PCBA has a molecular weight less than 10,000 g/mol. In some embodiments, PCBA has a molecular weight more than 50,000 g/mol.

In one embodiment, PCBG has a molecular weight from 5,000 to 15,000 g/mol. In one embodiment, PCBG has a molecular weight from 5,000 to 30,000 g/mol. In some embodiments, PCBG has a molecular weight less than 5,000 g/mol. In some embodiments, PCBG has a molecular weight more than 30,000 g/mol.

In one embodiment, PCBM has a molecular weight from 5,000 to 15,000 g/mol. In one embodiment, PCBM has a molecular weight from 5,000 to 30,000 g/mol. In some embodiments, PCBM has a molecular weight less than 5,000 g/mol. In some embodiments, PCBM has a molecular weight more than 30,000 g/mol.

In one embodiment, PCBO has a molecular weight from 10,000 to 20,000 g/mol. In one embodiment, PCBO has a molecular weight from 5,000 to 30,000 g/mol. In some embodiments, PCBO has a molecular weight less than 5,000 g/mol. In some embodiments, PCBO has a molecular weight more than 30,000 g/mol.

In one embodiment, PCBS has a molecular weight from 20,000 to 30,000 g/mol. In one embodiment, PCBS has a molecular weight from 10,000 to 50,000 g/mol. In some embodiments, PCBS has a molecular weight less than 10,000 g/mol. In some embodiments, PCBS has a molecular weight more than 50,000 g/mol.

In one embodiment, PCBT has a molecular weight from 20,000 to 30,000 g/mol. In one embodiment, PCBT has a molecular weight from 10,000 to 50,000 g/mol. In some embodiments, PCBT has a molecular weight less than 10,000 g/mol. In some embodiments, PCBT has a molecular weight more than 50,000 g/mol.

In one embodiment, PCBF has a molecular weight from 5,000 to 10,000 g/mol. In one embodiment, PCBF has a molecular weight from 5,000 to 20,000 g/mol. In some embodiments, PCBF has a molecular weight less than 5,000 g/mol. In some embodiments, PCBF has a molecular weight more than 20,000 g/mol.

In one embodiment, PCBC has a molecular weight from 20,000 to 30,000 g/mol. In one embodiment, PCBC has a molecular weight from 10,000 to 50,000 g/mol. In some embodiments, PCBC has a molecular weight less than 10,000 g/mol. In some embodiments, PCBC has a molecular weight more than 50,000 g/mol.

The thermal properties of the polyesters were analyzed using differential scanning calorimetry (DSC) under an N$_2$ atmosphere. The polyester samples were heated from 0 to 200° C. at a rate of 20° C./min. After this step, they were isothermally held at 200° C. for 5 min, then cooled to 0° C. at a rate of 20° C./min. DSC did not show a melting transition in any of the polymer samples, suggesting that all the materials are amorphous thermoplastics. The semi-rigid structure of the CBDO-1 monomer unit has a profound effect on the thermal properties such as, for example, the glass transition temperatures (T$_g$s) of the final polyesters. For instance, the substitution of the ethylene glycol unit with the cyclobutane unit increased the $T_g$s of the polymers. The $T_g$s of the polyesters derived from CBDO-1 and aliphatic diacids such as succinic acid (PCBS) and adipic acid (PCBA) were approximately 50° C. and 80° C. higher than their ethylene glycol analogs: polyethylene succinate and polyethylene adipate, respectively.

Figure 11:
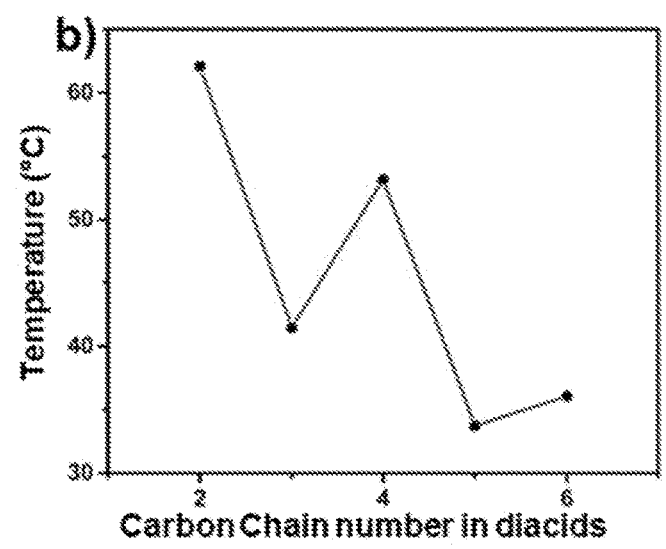
FIG. 11 is a plot of $T_g$s of polymers against carbon chain length of aliphatic diacids.

FIG. 11 is a plot of $T_g$s of polymers against carbon chain length of aliphatic diacids. FIG. 11 shows the effect of the carbon chain length of the diacid on the $T_g$ of the polyesters. This representation shows a considerable decrease in $T_g$ with an increasing length of the carbon chain of the diacid; PCBG was found to have the lowest $T_g$ of 33° C. amongst all the aliphatic polyesters tested while PCBO had the highest $T_g$ of 62° C. This decrease is attributed to the increase of chain mobility with higher flexible aliphatic content from 2-carbon oxalic acid to 6-carbon adipic acid. Interestingly, the polyesters with an even-numbered carbon chain (PCBO, PCBS, and PCBA) showed a higher $T_g$ than the polyesters with odd-numbered carbon chain (PCBM, PCBG). This odd-even difference in $T_g$s shows that the packing and stereochemical properties of the even-numbered carbon chain form a better-organized structure in a solid phase, which requires more energy to move apart.

Similarly, the introduction of CBDO-1 in conjunction with the rigid aromatic diacids also showed a clear impact on the $T_g$ of the polyesters. It was observed that the $T_g$s of polyesters synthesized from CBDO-1 with terephthalic acid (PCBT), and 2,5-furandicarboxylic acid (PCBF), were higher than those of the polyesters derived from aliphatic diacids, with PCBT and PCBF having $T_g$s of 114 and 109° C., respectively. It should be noted that PET (polyethylene terephthalate) and PEF (polyethylene 2,5-furandicarboxylate) synthesized under similar conditions were shown to have $T_g$s of 80° C. and 87° C., correspondingly, meaning that the replacement of flexible ethylene glycol with the semi-rigid CBDO-1 in the above two polymers improved their $T_g$s.

Moreover, incorporating a semi-rigid diacid, CBDA-1, boosts the $T_g$ of the polyester by 50° C. compared to those of the polyesters derived from the other aliphatic diacids. The $T_g$ of the polyester of CBDO-1 and CBDA-1 (PCBC) was 110° C., which suggests that the structure of the cyclobutane backbone together with the bulky and inflexible side group (i.e., phenyl) in both of the two monomers has a significant effect in modulating the $T_g$ of PCBC to a high value. The $T_g$s of the CBPs can also be tuned by changing their molecular weights.

Figure 12:
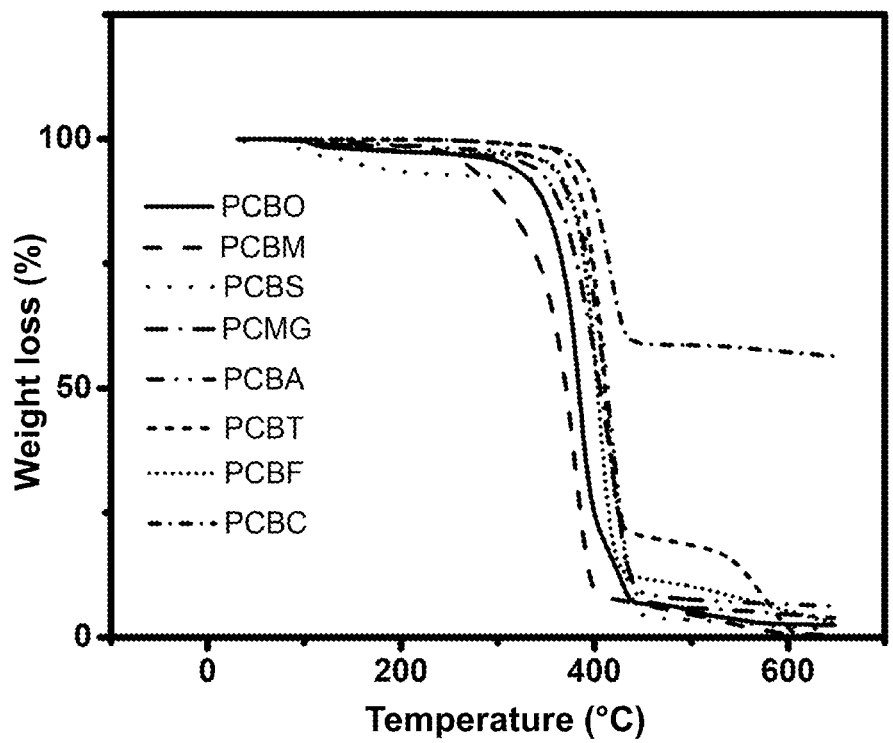
FIG. 12 is a TGA plot of CBDO-1 based polymers from 30 to 600° C.

FIG. 12 is a TGA plot of CBDO-1 based polymers from 30 to 600° C. heated at a rate of 20° C./min. under $N_2$.

Figure 13:
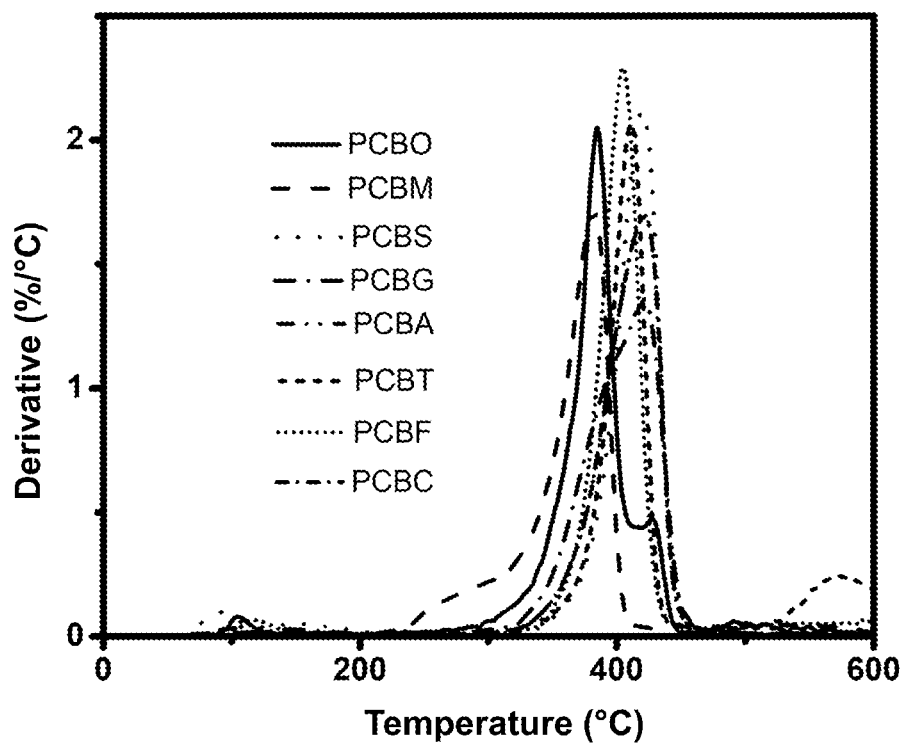
FIG. 13 is a plot of the derivative of the TGA traces (%/° C.) versus temperature.

FIG. 13 is a plot of the derivative of the TGA traces (%/° C.) versus temperature.

The thermal stabilities of the CBPs were examined by comparing the temperatures at which the onset of decomposition occurs, $T_{5\%}$ (5% weight loss), and maximum rate of decomposition $(T_d)$ occur. Thermogravimetric analysis (TGA) was employed to measure these characteristics under a $N_2$ atmosphere. As expected, the morphology of CBDO-1 does affect the decomposition temperatures of the synthesized polyesters. FIGS. 12 and 13 reveal that most of the CBPs derived from aliphatic diacids showed high thermal stability with substantially no weight loss below 300° C. PCBM exhibited an onset decomposition temperature ($T_{5\%}$) at 266° C., while PCBA exhibited the highest $T_{5\%}$ at 350° C. The thermal stability of CBPs increases slightly with the increase of the length of the linear diacids used in synthesizing the polyesters. In the case of the aromatic diacids, PCBT and PCBF showed similar $T_{5\%}$, 353° C. and 341° C., respectively. When the diacid monomer was replaced with semi-rigid CBDA-1, PCBC was obtained, which showed a $T_{5\%}$ of 383° C., which was highest among all the CBPs synthesized in this study. Notably, the maximum decomposition temperature $(T_d)$ of the CBPs were in the range of 380 to 420° C., without any significant difference as that of $T_{5\%}$, suggesting the decomposition of these polyesters might be governed by cleavage of cyclobutane moieties.

The CBDO-1 derived polymers synthesized and described herein have similar thermal properties compared to BPA. However, CBDO-1 does not have a phenol group, which is thought to enable BPA to trigger estrogenic pathways in the body. Furthermore, CBDO-1 is more reactive than TMCD, offering more flexibility to introduce functional groups and manufacture higher molecular weight polymers. As such, CBDO-1 may serve as a BPA replacement with reduced carcinogenic and disruptive endocrine effects.

Additionally, many of the diacids, such as succinic acid, 2,5-furandicarboxylic acid, and CBDA-1, used in the polyester syntheses can be produced from various biomass-derived precursors. The starting material for making CBDO-1, cinnamic acid, can also be obtained from glucose or Dried Distillers Grains with Solubles (DDGS), which is generated as a side product of dry mill ethanol production on a large scale and used as livestock feed. Due to the possible environmentally-friendly origin of the starting materials, the CBPs are greener compared to BPA-based petroleum derived polymers.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A polymer comprising:
   a plurality of repeated polymerized units according to scheme (2):

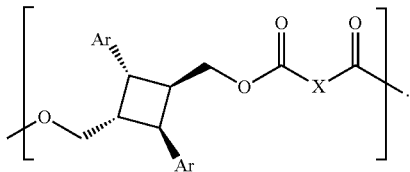

2. The polymer of claim 1, wherein X has less than 20 carbon atoms and is selected from the group consisting of an aliphatic chain, an aliphatic heterochain, a branched aliphatic chain, an aliphatic ring, an aromatic ring, a heterocyclic ring, and combinations thereof.

3. The polymer of claim 2, wherein X is selected from the group consisting of an aliphatic chain having 0-12 atoms, a 1,4-benzene ring, a 2,5-furan ring, and a 2,4-diphenyl-1,3-cyclobutane ring.

4. The polymer of claim 1, wherein Ar is a non-substituted aromatic ring and is selected from the group consisting of benzene, furan, thiophene, and pyridine.

5. The polymer of claim 1, wherein Ar is a substituted aromatic ring and wherein the substituents are selected from the group of methyl, methoxyl, hydroxyl, and halogens.

6. The polymer of claim 1, wherein the polymer is stereospecific.

7. The polymer of claim 1, wherein the polymer is a mixture of stereo isomers.

8. The polymer of claim 1, wherein the polymer is selected from the group consisting of polycyclobutane oxalate (PCBO), polycyclobutane malonate (PCBM), polycyclobutane succinate (PCBS), polycyclobutane glutarate (PCBG), polycyclobutane adipate (PCBA), polycyclobutane terephthalate (PCBT), polycyclobutane furandicarboxylate (PCBF), and polycyclobutane-1,3-cyclobutane-dicarboxylate (PCBC).

9. A method of making a polymer comprising:
dimerizing trans-cinnamic acid, forming CBDA-1;
reducing CBDA-1, forming CBDO-1;
condensing CBDO-1 with a diacid, forming monomeric subunits; and
polymerizing the monomeric subunits together to form the polymer.

10. The method of claim 9, wherein dimerizing trans-cinnamic acid, forming CBDA-1, proceeds via a [2+2] photocyclization reaction in a brine slurry.

11. The method of claim 9, wherein reducing CBDA-1, forming CBDO-1 is done using a compound selected from the group consisting of $NaBH_4$ in the presence of $I_2$, $BH_3$ in THF, $LiAlH_4$, and catalytic hydrogenation in the presence of zinc, zinc oxide, copper, copper oxide, chromium, chromium oxide, iron, iron oxide, nickel, nickel oxide, cobalt, cobalt oxide, palladium, palladium oxide, iridium, iridium oxide, ruthenium, ruthenium oxide, rhenium, rhenium oxide, molybdenum, molybdenum oxide, platinum, platinum oxide, and combinations thereof.

12. The method of claim 9, wherein condensing CBDO-1 with a diacid is done using polycondensation catalysts such as metal oxides or salts of silicon, aluminum, zinc, lead, zirconium, antimony, cobalt, and alkoxide, organometallic compounds of tin, lead, titanium, and tetravalent hafnium compounds.

13. A polymer comprising:
a plurality of repeated polymerized units according to scheme (2):

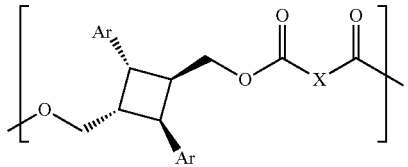

wherein Ar is benzene and wherein X is selected from the group consisting of an aliphatic chain with 0-12 atoms, a 1,4-benzene ring, a 2,5-furan ring, and a 2,4-diphenyl-1,3-cyclobutane ring.

14. The polymer of claim 13, wherein the formed polymer is selected from the group consisting of polycyclobutane oxalate (PCBO), polycyclobutane malonate (PCBM), polycyclobutane succinate (PCBS), polycyclobutane glutarate (PCBG), polycyclobutane adipate (PCBA), polycyclobutane terephthalate (PCBT), polycyclobutane furandicarboxylate (PCBF), and polycyclobutane-1,3-cyclobutane-dicarboxylate (PCBC).

* * * * *